US006774081B1

(12) United States Patent
Datta et al.

(10) Patent No.: US 6,774,081 B1
(45) Date of Patent: Aug. 10, 2004

(54) PROCESS FOR PREPARING VANADYL PYROPHOSPHATE CATALYST

(75) Inventors: Arunabha Datta, Dehradun (IN); Soumen Dasgupta, Dehradun (IN); Monika Agarwal, Dehradun (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/393,401

(22) Filed: Mar. 20, 2003

(51) Int. Cl.$^7$ .................... B01J 27/14; B01J 27/198; C01B 15/16; C01B 25/26
(52) U.S. Cl. .............. 502/208; 502/209; 423/305; 423/306
(58) Field of Search .................. 502/208, 209; 423/305, 306

(56) References Cited

U.S. PATENT DOCUMENTS

| 4,392,986 A | * | 7/1983 | Yang et al. | .............. 502/209 |
|---|---|---|---|---|
| 4,517,371 A | * | 5/1985 | Yang et al. | .............. 549/239 |
| 4,520,127 A | * | 5/1985 | Otake et al. | .............. 502/209 |
| 4,569,925 A | * | 2/1986 | Yang et al. | .............. 502/209 |

FOREIGN PATENT DOCUMENTS

| JP | 0510990 | 4/1993 |
|---|---|---|
| SU | 1409590 | * 7/1988 ........... C01B/25/38 |

OTHER PUBLICATIONS

English Abstract of JP 05 103990A, Apr. 27, 1993, Database WPI, Section Ch.Week 199321. Derwent Pub. Ltd. XP002243362.

Horowitz. H.S. et al. "V–P–O Catalysts for Oxidation of Butane to Maleic Anhydride. Influence of $(VO)_2H_4P_2O_9$ Precursor Morphology on Catalytic Properties," *Applied Catalysis* (1988) 38;pp 193–210.

Mizuno, Noritaka et al. "One–Pot Synthesis of $VOHPO_4$–O, $5H_2O$ with High Growth of the (001) Plane: An Important Catalyst Precursor of $(VO)_2P_2O_7$," *Chem. Mater.* (1997), 9: pp 2697–2698.

Hutchings, G.J. and Raymond Higgins. "Selective oxidation of n–butane to maleic anhydride with vanadium phosphorus catalysts prepared by comminution in the presence of dispersants." *Applied Catalysis A: General*, (1997), 154: pp 103–115.

* cited by examiner

Primary Examiner—Mark L. Bell
Assistant Examiner—Patricia L. Hailey
(74) Attorney, Agent, or Firm—Ladas & Parry

(57) ABSTRACT

The present invention relates to a process for preparing vanadyl pyrophosphate catalyst with improved structural characteristics for the selective oxidation of butane to maleic anhydride.

13 Claims, 1 Drawing Sheet

Figure 1:
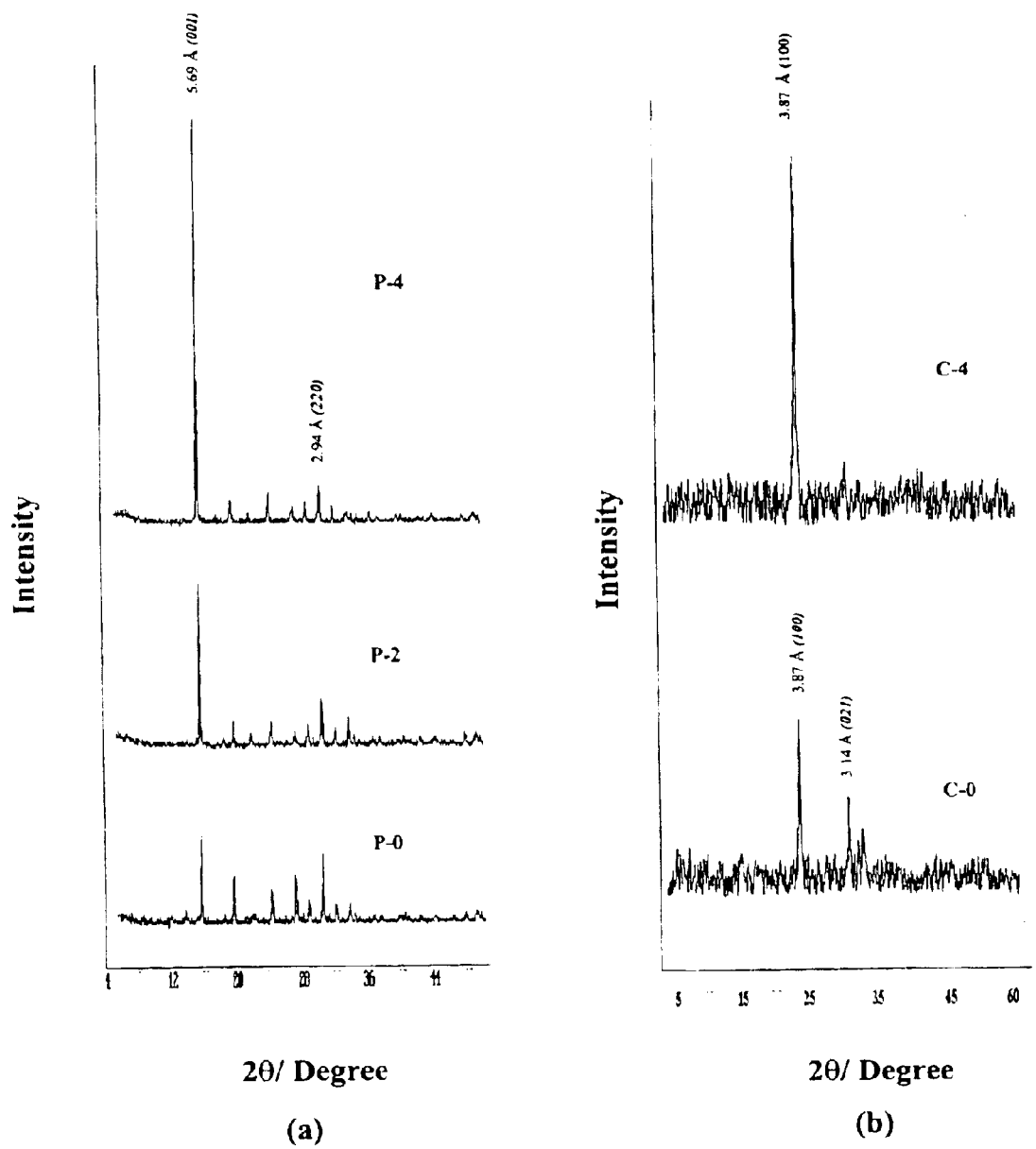

2θ/ Degree
(a)

2θ/ Degree
(b)

PROCESS FOR PREPARING VANADYL PYROPHOSPHATE CATALYST

FIELD OF THE INVENTION

The present invention relates to a process for preparing vanadyl pyrophosphate catalyst. More particularly, the present invention relates to a process for the preparation of vanadyl pyrophosphate catalyst with improved structural characteristics for the selective oxidation of butane to maleic anhydride.

BACKGROUND OF THE INVENTION

Layered vanadyl hydrogen phosphate hemihydrate, $VOHPO_4.0.5H_2O$ has tremendous technological importance as the precursor to the vanadyl pyrophosphate, $(VO)_2P_2O_7$ which is used as the catalyst for the commercially established selective oxidation of butane to maleic anhydride [Ref. G. Centi, F. Trifiro, J. R. Ebner, V. M. Franchetti, Chem.Rev.,1988, vol. 58, p 55].

Maleic anhydride is a valuable intermediate for the production of some commercially important fine chemicals and polymers. The largest use of maleic anhydride occurs in the production of unsaturated polyesters. In the fine chemicals industry, maleic anhydride is used as a raw material for the production of succinic anhydride. γ-butyrolactone, 1,4-butanediol, tetrahydrofuran, fumaric acid, malic acid and D-L tartaric acid.

Vanadyl pyrophosphate $(VO)_2P_2O_7$ catalyzed process of maleic anhydride synthesis by selective oxidation of butane replaced the earlier process of gas phase oxidation of benzene on a supported V—Mo—O catalyst due to economic and environmental reasons. Under typical industrial conditions 65–70% selectivity towards maleic anhydride is achieved for butane conversion of 70–85%. Carbondioxide and trace amounts of acetic acid are the only other byproducts.

Vanadyl pyrophosphate $(VO)_2P_2O_7$ is regarded to be the active phase of the VPO catalyst since it is the only bulk phase that exists in equilibrated VPO catalysts. The catalytic activity of $(VO)_2P_2O_7$ is known to be sensitive to its morphological characteristics and in particular the preferential exposure of the (100) crystallographic plane of the $(VO)_2P_2O_7$ crystallites is highly desirable since this plane has been established to be the most active and selective for the oxidation of butane to maleic anhydride [Ref. "Vanadyl Pyrophosphate Catalysts". ed. G. Centi, Catal.Today, 1993, vol. 16]. The morphology of the $VO_2P_2O_7$ phase is indirectly controlled through that of the $VOHPO_4.0.5H_2O$ phase, since it undergoes a topotactic transformation at ~450° C. to the $(VO)_2P_2O_7$ phase with retention of the microstructure and morphological characteristics of the precursor $VOHPO_4.0.5H_2O$ phase [Ref. J. W. Johnson, D. C. Johnston, A. J. Jacobson, J. F. Brody, J. Am. Chem. Soc., 1984, vol. 106, p. 8123]. During this transformation the (001) plane of $VOHPO_4.0.5H_2O$ is transformed to the active (100) plane of $(VO)_2P_2O_7$ with retention of the morphology/surface defect of the (001) plane of the hemihydrate phase.

In view of the well established role of the (100) plane of the $(VO)_2P_2O_7$ phase in catalyzing the selective oxidation of butane to maleic anhydride, the synthesis of phases with preferential exposure of this plane would be of great significance in increasing the activity of $(VO)_2P_2O_7$ catalyst. The intensity ratio of the interplaner (100) and in-plane (021) x-ray reflection of $(VO)_2P_2O_7$ i.e. $(I_{100}:I_{021})$ is used to determine the preferential exposure of the surface (100) planes proposed to contain the active and selective catalytic sites for selective oxidation of butane to maleic anhydride. The conventional methods of synthesis of $(VO)_2P_2O_7$ catalysts typically exhibits low intensity ratios $I_{100}:I_{021}$ ca. 0.4–2 indicating that the surface (100) planes are not preferentially exposed by these methods [Ref. V. V. Guliants, J. B. Benziger, S. Sundaresan, I. E. Wachs, J. M. Jehng, J. E. Roberts, Catal. Today, 1996, vol. 28, p. 275].

There are very few reports in literature on the preferential exposure of catalytically important (100) crystallographic plane of $(VO)_2P_2O_7$ phase.

Reference is made to a procedure of one pot synthesis of $VOHPO_4.0.5H_2O$ with high growth of the (001) plane and its subsequent transformation to a $(VO)_2P_2O_7$ phase with preferentially exposed (100) plane [N. Mizuno, H. Hatayama, M. Misono, Chem. Mater., 1997, vol. 9, no. 12, p. 2697]. The drawback of this procedure is the requirement of a costly surfactant and hydrothermal condition during the crystallization of the precursor $VOHPO_4.0.5H_2O$ phase.

Reference is made to colloidal templated synthesis of $(VO)_2P_2O_7$ phase [M. A. Carreon, V. V. Guliants, Chem.Commun., 2001, p 1438] with $I_{100}:I_{021}=2.48$ suggesting preferential exposure of surface (100) planes. However, this method comprises a complex procedure using mono dispersed polystyrene spheres as templating agents for formation of $VO)_2P_2O_7$ with selectively exposed catalytically important (100) plane.

OBJECTS OF THE INVENTION

The main object of the invention is to provide a process for the preparation of vanadyl pyrophosphate catalysts with improved structural characteristics for the selective oxidation of butane to maleic anhydride.

Another object of the invention is to provide a simple method for the selective exposure of catalytically active (100) plane of the $(VO)_2P_2O_7$ catalyst used for selective oxidation of butane to maleic anhydride.

Yet another object of the invention is to provide a process for the preparation of vanadyl pyrophosphate catalyst which exhibits high selective exposure of the catalytically active (100) plane in the $(VO)_2P_2O_7$ catalyst in comparison to catalyst prepared by conventional methods.

It is another object of the invention to provide a process for the preparation of vanadyl pyrophosphate which does not require hydrothermal reaction conditions for the preparation of $(VO)_2P_2O_7$ catalyst with selective exposure of the catalytically important (100) plane.

It is further object of the invention to provide a process for the preparation of vanadyl pyrophosphate which does not require costly surfactant and mono dispersed colloidal templating agents during the preparation of $(VO)_2P_2O_7$ catalyst with selectively exposed (100) plane.

SUMMARY OF THE INVENTION

Accordingly the present invention provides a process for the preparation of vanadyl pyrophosphate catalyst with improved structural characteristics and useful for the selective oxidation of butane to maleic anhydride, which comprises:

i) reducing $V_2O_5$ solid by an aqueous solution of $NH_2OH.HCl$ in the presence of $H_3PO_4$ to obtain a blue solution, ii) evaporating the solution to obtain a pasty mass, iii) aging the pasty mass to obtain a blue solid, iv) washing the solid with boiling water to remove the water soluble phases, v) drying the solid to form $VOHPO_4 \cdot 0.5H_2O$ phase, vi) grinding the dry $VOHPO_4 \cdot 0.5H_2O$ phase to a fine powder.

vii) dispersing the $VOHPO_4 \cdot 0.5H_2O$ powder into a mixture of dimethyl formamide (DMMF) and water ($H_2O$) and stirring the resulting slurry, viii) recovering the dispersed $VOHPO_4 \cdot 0.5H_2O$ powder from the slurry and washing with hot water, ix) drying the powder to obtain a $VOHPO_4 \cdot 0.5H_2O$ solid with selectively enhanced (001) plane, x) calcining the $VOHPO_4 \cdot 0.5H_2O$ solid with selectively enhanced (001) plane to obtain the desired $(VO)_2P_2O_7$ phase with selectively exposed (100) plane.

In one embodiment of the invention. $V_2O_5$ solid is reduced in step (i) at a temperature in the range of 70–100° C. while maintaining a P:V ratio in the reaction mixture in the range of 1:0.8 to 1:1.4.

In another embodiment of the invention, the pasty mass obtained in step (ii) is aged in step (iii) by heating to a temperature in the range of 100–150° C. in air atmosphere for a period in the range of 12–36 hours.

In yet another embodiment of the invention, the washed solid obtained in step (iv) is dried in step (v) at a temperature in the range of 100–150° C. for 6–16 hours in air atmosphere to form $VOHPO_4 \cdot 0.5H_2O$ phase.

In yet another embodiment of the invention, the dry $VOHPO_4 \cdot 0.5H_2O$ powder obtained in step (vi) is dispersed in step (vii) in a mixture of dimethyl formamide (DMF) and water ($H_2O$) wherein the DMF to $H_2O$ ratio is in the range of 20:1–1:20 (v/v) and the resulting to slurry is stirred for 1–6 hours at a temperature in the range of 50–100° C., In another embodiment of the invention, the dispersed $VOHPO_4 \cdot 0.5H_2O$ powder is recovered from the slurry of step (vii) by filtration.

In yet another embodiment of the invention, the $VOHPO_4 \cdot 0.5H_2O$ solid with selectively enhanced (001) plane obtained at the end of step (ix) is calcined in step (x) at a temperature in the range of 400–500° C. under flowing nitrogen, at flow rate of 6–10 liter/hour for 1–6 hours to obtain desired $(VO)_2P_2O_7$ phase with selectively exposed (100) plane.

In another embodiment of the invention the ratio of DMF to $H_2O$ used in the mixture of DMF and $H_2O$ is preferably in the range of 2:1–1:2 (v/v).

In another embodiment of the invention, the temperature during stirring of $VOHPO_4 \cdot 0.5H_2O$ powder in DMF-$H_2O$ mixture is preferably in the range of 75–90° C.

In another embodiment of the invention, the $VOHPO_4 \cdot 0.5H_2O$ solid obtained shows selective exposure of the (001) plane.

In another embodiment of the invention, selective exposure of the (001) plane in $VOHPO_4 \cdot 0.5H_2O$ can be varied b) changing the duration of DMF-$H_2O$ treatment.

In another embodiment of the invention, the temperature used in calcination of $VOHPO_4 \cdot 0.5H_2O$ solid is in the range of 450–470° C. with a gradual increase of temperature at a rate of 1–2° C./minute under flowing nitrogen.

In another embodiment of the invention, the $(VO)_2P_2O_7$ obtained shows enhanced exposure of the (100) plane and is catalytically active for the selective oxidation of butane to maleic anhydride.

BRIEF DESCRIPTION OF THE ACCOMPANYING DRAWING

FIG. 1a shows XRD pattern of the as synthesized $VOHPO_4 \cdot 0.5H_2O$ phase (sample code P-0) and the $VOHPO_4 \cdot 0.5H_2O$ phases obtained after stirring of the as synthesized $VOHPO_4 \cdot 0.5H_2O$ phase in DMF-$H_2O$ mixture at 80° C. for 2 hours (sample code P-2) and 4 hours (sample code P-4), indicating selective exposure of the (001) plane topotactically related to the catalytically important (100) plane of the $(VO)_2P_2O_7$ catalyst FIG. 1b shows XRD pattern of $(VO)_2O_7$ phase (sample code C-0) obtained by thermal topotactic transformation of the as synthesized precursor $VOHPO_4 \cdot 0.5H_2O$ (P-0) and the XRD of the $(VO)_2P_2O_7$ phase (sample code C-4) obtained by transformation of the precursor P-4 (defined in table 1) showing selective exposure of the (100) plane in the $(VO)_2P_2O_7$ phase transformed from DMF-$H_2O$ treated $VOHPO_4 \cdot 0.5H_2O$ precursor.

DETAILED DESCRIPTION OF THE INVENTION

The present invention provides a process for the preparation of vanadyl pyrophosphate catalyst with improved structural characteristics and useful for the selective oxidation of butane to maleic anhydride. The process of the invention comprises reducing $V_2O_5$ solid by an aqueous solution of $NH_2OH \cdot HCl$ in the presence of $H_3PO_4$ to obtain a blue solution w, evaporating the solution to obtain a pasty mass, aging the pasty mass to obtain a blue solid, washing the solid with boiling water to remove the water soluble phases, drying the solid to form $VOHPO_4 \cdot 0.5H_2O$ phase, grinding the dry $VOHPO_4 \cdot 0.5H_2O$ phase to a fine powder, dispersing the $VOHPO_4 \cdot 0.5H_2O$ powder into a mixture of dimethyl formamide (DMF) and water ($H_2O$) and stirring the resulting slurry, recovering the dispersed $VOHPO_4 \cdot 0.5H_2O$ powder from the slurry and washing with hot water, drying the powder to obtain a $VOHPO_4 \cdot 0.5H_2O$ solid with selectively enhanced (001) plane, calcining the $VOHPO_4 \cdot 0.5H_2O$ solid with selectively enhanced (001) plane to obtain the desired $(VO)_2P_2O_7$ phase with selectively exposed (100) plane.

The $V_2O_5$ solid is reduced in step (i) preferably at a temperature in the range of 70–100° C. while maintaining a P:V ratio in the reaction mixture in the range of 1:0.8 to 1:1.4. The pasty mass obtained in step (ii) is aged in step (iii) by heating to a temperature in the range of 100–150° C. in air atmosphere for a period in the range of 12–36 hours. The washed solid obtained in step (iv) is dried in step (v) preferably at a temperature in the range of 100–150° C. for 6–16 hours in air atmosphere to form $VOHPO_4 \cdot 0.5H_2O$ phase. The dry $VOHPO_4 \cdot 0.5H_2O$ powder obtained in step (vi) is dispersed in step (vii) in a mixture of dimethyl formamide (DMF) and water ($H_2O$) with DMF to $H_2O$ ratio in range of 20:1–1:20 (v/v). The resulting slurry is stirred for 1–6 hours at a temperature in the range of 50–100° C. Dispersed $VOHPO_4 \cdot 0.5H_2O$ powder is then recovered from slurry of step (vii) by filtration.

The $VOHPO_4 \cdot 0.5H_2O$ solid with selectively enhanced (001) plane obtained at the end of step (ix) is calcined in step (x) preferably at a temperature in the range of 400–500° C. under flowing nitrogen, at flow rate of 6–10 liter/hour for 1–6 hours to obtain desired $(VO)_2P_2O_7$ phase with selectively exposed (100) plane. The ratio of DMF to $H_2O$ used in the mixture of DMF and $H_2O$ is preferably in the range of 2:1–1:2 (v/v). The temperature during stirring of $VOHPO_4 \cdot 0.5H_2O$ powder in DMF-$H_2O$ mixture is preferably in the range of 75–90° C. The $VOHPO_4 \cdot 0.5H_2O$ solid obtained shows selective exposure of the (001) plane. Selective exposure of the (001) plane in $VOHPO_4 \cdot 0.5H_2O$ can be varied by changing duration of DMF-$H_2O$ treatment. The temperature used in calcination of $VOHPO_4 \cdot 0.5H_2O$ solid is in the range of 450–470° C. with a gradual increase of temperature at the rate of 1–2° C./minute under flowing nitrogen.

The $(VO)_2P_2O_7$ obtained shows enhanced exposure of the (100) plane and is catalytically active for the selective oxidation of butane to maleic anhydride. In the present invention infrared spectra (FTIR), thermo-gravimetric analysis (TGA) and elemental analysis showed no structural changes in $VOHPO_4.0.5H_2O$ solid following its treatment in $DMF-H_2O$ solvent mixture. X-ray diffraction analysis of the $(VO)_2P_2O_7$ phases, obtained by thermal transformation of the $VOHPO_4.0.5H_2O$ phase with $DMF-H_2O$ treatment, shows a 4 to 8 fold increase of the ratio of intensity of the most prominent (100) line to the next most prominent (021) line, i.e. $I_{100}/I_{021}$ in comparison to the $(VO)_2P_2O_7$ phase obtained by thermal transformation of the $VOHPO_4.0.5H_2O$ solid without any $DMF-H_2O$ treatment.

The following representative example is given by way of illustration and therefore should not be construed to limit the scope of the present invention.

EXAMPLE

Step 1

3.475 grams (0.05 moles) of hydroxylamine hydrochloride (99.99 % purity, Sigma) was dissolved in laboratory-distilled water (150 ml). Into this solution, 4.545 grams (0.025 moles) vanadium pentoxide (99.99% purity, Sigma) powder was dispersed followed by 5.76 grams (0.05 moles) of 85% phosphoric acid (Sigma) and the slurry magnetically stirred at 80° C. for 2 hours. During this time the orange yellow slurry gradually turned into an ink blue solution. This solution was evaporated to a blue pasty mass and aged in an air oven at 120° C. for 16 hours. The sky blue solid obtained was finely ground and the powder rinsed several times with boiled distilled water till no chloride ion was detected in the washing. The solid was dried in an air oven at 120° C. for 16 hours. XRD, elemental analysis and FTIR characterization confirmed the formation of pure $VOHPO_4.0.5H_2O$ phase.

Step 2

Two gm quantity of $VOHPO_4.0.5H_2O$ prepared in step 1 was dispersed into a 30-ml. mixture of 1:1 volume/volume dimethyl formamide (99% purity, Ranbaxy Chemicals) and laboratory-distilled water. The slurry was stirred at 80° C. for 2 hours. The solid was isolated by filtration, washed thoroughly with warm water and dried in an air oven at 120° C. for 6 hours. XRD showed selective enhancement of the intensity of the (001) reflection of $VOHPO_4.0.5H_2O$. Thus the ratio of the intensity due to the (001) and the next most intense (220) reflection in $VOHPO_4.0.5H_2O$ increased from 1.4 to 10 on $DMF-H_2O$ treatment for 2 hours indicating selectively enhanced exposure of the (001) plane of $VOHPO_4.0.5H_2O$.

Step 3

One-gram quantity of $DMF-H_2O$ treated $VOHPO_4.0.5H_2O$ solid with selectivity exposed (001) plane and the parent $VOHPO_4.0.5H_2O$ solid without $DMF-H_2O$ treatment was calcined at 450° C. in a furnace for 2 hours. The calcination temperature was gradually attained at a linear rate of 2° C./minute. Throughout the heating process dry nitrogen was continuously passed over the solids. XRD of the brown solids obtained shows the formation of pure $(VO)_2P_2O_7$ phase in both the cases. The intensity ratio of (100) and the next intense (021) reflection i.e. $I_{100}/I_{021}$ increased from 2 in the $(VO)_2P_2O_7$ phase obtained by thermal transformation of the $VOHPO_4.0.5H_2O$ phase without $DMF-H_2O$ treatment to 10.8 in the $(VO)_2P_2O_7$ phase obtained by thermal transformation of the $VOHPO_4.0.5H_2O$ phase, stirred in $DMF-H_2O$ mixture for 2 hours, showing higher selective exposure of the (100) planes in the later phase.

TABLE 1

Intensity ratio of XRD lines due to (001) and (220) reflection i.e. $I_{001}/I_{220}$ of as synthesized $VOHPO_4.0.5H_2O$ (sample code P-0) and $VOHPO_4.0.5H_2O$ stirred in 1:1 V/V $DMF-H_2O$ mixture at 80° C. for different durations.

| Sample Code | Duration of stirring In hours) | $I_{001}/I_{220}$ |
|---|---|---|
| P-0 | 0 | 1.4 |
| P-1 | 1 | 8 |
| P-2 | 2 | 10 |
| P-4 | 4 | 14 |
| P-6 | 6 | 14.5 |

TABLE 2

Intensity ratio of XRD lines due to (100) and (021) reflection i.e. $I_{100}/I_{021}$ of $(VO)_2P_2O_7$ phase transformed from as synthesized $VOHPO_4.0.5H_2O$ (sample code C-0) and from $VOHPO_4.0.5H_2O$ precursor stirred in 1:1 volume/volume $DMF-H_2O$ mixture at 80° C. for different durations.

| Sample Code | Duration of stirring of the precursor in $DMF-H_2O$ mixture. (In hours) | $I_{100}/I_{021}$ |
|---|---|---|
| C-0 | 0 | 2 |
| C-1 | 1 | 8.5 |
| C-2 | 2 | 10.8 |
| C-4 | 4 | 12 |
| C-6 | 6 | 12.4 |

FIG. 1a shows XRD pattern of the as synthesized $VOHPO_4.0.5H_2O$ phase (sample code P-0) and the $VOHPO_4.0.5H_2O$ phases obtained after stirring of the as synthesized $VOHPO_4.0.5H_2O$ phase in $DMF-H_2O$ mixture at 80° C. for 2 hours (sample code P-2) and 4 hours (sample code P-4), indicating selective exposure of the (001) plane topotactically related to the catalytically important (100) plane of the $(VO)_2P_2O_7$ catalyst.

FIG. 1b shows XRD pattern of $(VO)_2P_2O_7$ phase (sample code COO) obtained by thermal topotactic transformation of the as synthesized precursor $VOHPO_4.0.5H_2O$ (P) and the XRD of the $(VO)_2P_2O_7$ phase (sample code C-4) obtained by transformation of the precursor P-4 (defined in table 1) showing selective exposure of the (100) plane in the $(VO)_2P_2O_7$ phase transformed from $DMF-H_2O$ treated $VOHPO_4.0.5H_2O$ precursor.

The main advantages of the present invention are:

1. The process of the present invention provides a simple method for selective exposure of the catalytically active (100) plane of the $(VO)_2P_2O_7$ catalyst used for the selective oxidation of butane to maleic anhydride.

2. The present process demonstrate that by a simple post synthetic solvent treatment in $DMF-H_2O$ or $DMSO-H_2O$ mixture, the growth of the (001) plane of the $VOHPO_4.0.5H_2O$ phase can be selectivity enhanced which subsequently can be translated by a thermal topotactic transformation to the selective growth of the catalytically active (100) plane of the $(VO)_2P_2O_7$ phase.

3. The conventional $(VO)_2P_2O_7$ catalyst typically exhibited low intensity ratio $I_{100}/I_{021}$ ca. 0.4–2 whereas the process described achieves $I_{100}/I_{021}$ ratio ca. 8–12 indicating higher selective exposure of the catalytically active (100) plane in the $(VO)_2P_2O_7$ catalyst in comparison to the conventional preparation methods.

4. The present process does not require hydrothermal reaction conditions for the preparation of $(VO)_2P_2O_7$ catalyst with selective exposure of the catalytically important (100) plane.

5. The present process does not require costly surfactant and mono dispersed colloidal templating agents during the preparation of $(VO)_2P_2O_7$ catalyst with selectively exposed (100) plane.

We claim:

1. A process for the preparation of vanadyl pyrophosphate catalyst with improved structural characteristics and useful for the selective oxidation of butane to maleic anhydride, which comprises:

(i) reducing $V_2O_5$ solid by an aqueous solution of $NH_2OH.HCl$ in the presence of $H_3PO_4$ to obtain a blue solution, (ii) evaporating the solution to obtain a pasty mass, (iii) aging the pasty mass to obtain a blue solid, (iv) washing the solid with boiling water to remove the water soluble phases, (v) drying the solid to form $VOHPO_4.0.5H_2O$ phase, (vi) grinding the dry $VOHPO_4.0.5H_2O$ phase to a fine powder, (vii) dispersing the $VOHPO_4.0.5H_2O$ powder into a mixture of dimethyl formamide (DMF) and water ($H_2O$) and stirring the resulting slurry, (viii) recovering the dispersed $VOHPO_4.0.5H_2O$ powder from the slurry and washing with hot water, (ix) drying the powder to obtain a $VOHPO_4.0.5H_2O$ solid with selectively enhanced (001) plane, (x) calcining the $VOHPO_4.0.5H_2O$ solid with selectively enhanced (001) plane to obtain the desired $(VO)_2P_2O_7$ phase with selectively exposed (100) plane.

2. A process as claimed in claim 1 wherein the $V_2O_5$ solid is reduced in step (i) at a temperature in the range of 70–100° C. while maintaining a P:V ratio in the reaction mixture in the range of 1:0.8 to 1:1.4.

3. A process as claimed in claim 1 wherein the pasty mass obtained in step (ii) is aged in step (iii) by heating to a temperature in the range of 100–150° C. in air atmosphere for a period in the range of 12–36 hours.

4. A process as claimed in claim 1 wherein the washed solid obtained in step (iv) is dried in step (v) at a temperature in the range of 100–150° C. for 6–16 hours in air atmosphere to form $VOHPO_4.0.5H_2O$ phase.

5. A process as claimed in claim 1 wherein the dry $VOHPO_4.0.5H_2O$ powder obtained in step (vi) is dispersed in step (vii) in a mixture of dimethyl formamide (DMF) and water ($H_2O$) wherein the DMF to $H_2O$ ratio is in the range of 20:1–1:20 (v/v) and the resulting slurry is stirred for 1–6 hours at a temperature in the range of 50–100° C.

6. A process as claimed in claim 1 wherein the dispersed $VOHPO_4.0.5H_2O$ powder is recovered from the slurry of step (vii) by filtration.

7. A process as claimed in claim 1 wherein the $VOHPO_4.0.5H_2O$ solid with selectively enhanced (001) plane obtained at the end of step (ix) is calcined in step (x) at a temperature in the range of 400–500° C. under flowing nitrogen, at flow rate of 6–10 liter/hour for 1–6 hours to obtain $(VO)_2P_{27}$ phase with selectively exposed (100) plane.

8. A process as claimed in claim 1 wherein the ratio of DMF to $H_2O$ used in the mixture of DMF and $H_2O$ is in the range of 2:1–1:2 (v/v).

9. A process as claimed in claim 1 wherein the temperature during stirring of $VOHPO_4.0.5H_2O$ powder in DMF-$H_2O$ mixture is in the range of 75–90° C.

10. A process as claimed in claim 1 wherein the $VOHPO_4.0.5H_2O$ solid obtained shows selective exposure of the (001) plane.

11. A process as claimed in claim 1 wherein the selective exposure of the (001) plane in $VOHPO40.5H_2O$ is varied by changing the duration of DMF-$H_2O$ treatment.

12. A process as claimed in claim 1 wherein the temperature used in calcination of $VOHPO_4.0.5H_2O$ solid is in the range of 450–470° C. with a gradual increase of temperature at a rate of 1–2° C./minute under flowing nitrogen.

13. A process as claimed in claim 1 wherein the $(VO)_2P_2O_7$ obtained shows enhanced exposure of the (100) plane and is catalytically active for the selective oxidation of butane to maleic anhydride.

* * * * *